United States Patent
Wolters et al.

(10) Patent No.: US 11,821,824 B2
(45) Date of Patent: Nov. 21, 2023

(54) CELL SEPARATION APPARATUS

(71) Applicant: Koligo Therapeutics, Inc., New Albany, IN (US)

(72) Inventors: Rolf Wolters, Kailua, HI (US); Anthony Yang, Honolulu, HI (US); Josh Nelson, Kaleohe, HI (US); Stuart K. Williams, Harrods Creek, KY (US)

(73) Assignee: TISSUE GENESIS INTERNATIONAL LLC, Leander, TX (US)

( * ) Notice: Subject to any disclaimer, the term of this patent is extended or adjusted under 35 U.S.C. 154(b) by 1681 days.

(21) Appl. No.: 15/707,270

(22) Filed: Sep. 18, 2017

(65) Prior Publication Data
US 2018/0002666 A1   Jan. 4, 2018

Related U.S. Application Data

(63) Continuation-in-part of application No. 14/221,272, filed on Mar. 20, 2014, now abandoned, which is a continuation-in-part of application No. 13/844,548, filed on Mar. 15, 2013, now abandoned.

(60) Provisional application No. 61/703,742, filed on Sep. 20, 2012.

(51) Int. Cl.
| | |
|---|---|
| *C12M 3/00* | (2006.01) |
| *B01L 3/00* | (2006.01) |
| *A61M 1/00* | (2006.01) |
| *G01N 1/34* | (2006.01) |
| *C12N 5/077* | (2010.01) |
| *G01N 1/40* | (2006.01) |
| *C12N 5/0775* | (2010.01) |
| *A61K 35/35* | (2015.01) |
| *C12M 1/34* | (2006.01) |

(52) U.S. Cl.
CPC ............... *G01N 1/34* (2013.01); *A61K 35/35* (2013.01); *A61M 1/79* (2021.05); *C12M 41/00* (2013.01); *C12N 5/0653* (2013.01); *C12N 5/0667* (2013.01); *G01N 1/4044* (2013.01); *A61M 1/73* (2021.05); *A61M 2202/0014* (2013.01); *A61M 2202/0071* (2013.01); *A61M 2202/0085* (2013.01); *A61M 2202/08* (2013.01); *A61M 2202/09* (2013.01); *C12N 2509/10* (2013.01)

(58) Field of Classification Search
CPC ..................... C12M 41/00; C12N 2509/10
See application file for complete search history.

(56) References Cited

U.S. PATENT DOCUMENTS

| | | | | |
|---|---|---|---|---|
| 5,043,082 | A | * 8/1991 | Hermann, Jr. | ......... B01D 61/18 210/477 |
| 5,139,031 | A | * 8/1992 | Guirguis | ................ A61B 5/153 600/584 |
| 2004/0097829 | A1 | 5/2004 | McRury et al. | |
| 2004/0106195 | A1 | 6/2004 | Keller et al. | |
| | | (Continued) | | |

*Primary Examiner* — Nathan A Bowers
(74) *Attorney, Agent, or Firm* — Mark S. Cohen; PEARL COHEN ZEDEK LATZER BARATZ LLP

(57) ABSTRACT

Systems and methods herein are directed towards the separation of biologic material to obtain a target cell volume and/or cell concentration for harvesting. The target volume and/or concentration of cells may be obtained through a single cycle via three chambers, or by repeated cycles through one or more chambers to dilute the digestive enzymes used in the process and concentrate the harvestable cell volume to a predetermined target.

20 Claims, 7 Drawing Sheets

(56) References Cited

U.S. PATENT DOCUMENTS

| | | |
|---|---|---|
| 2005/0058632 A1 | 3/2005 | Hedrick et al. |
| 2005/0084961 A1 | 4/2005 | Hedrick et al. |
| 2005/0123895 A1* | 6/2005 | Freund ............... B01D 17/0217 |
| | | 436/164 |
| 2007/0100277 A1 | 5/2007 | Shipped |
| 2009/0181450 A1* | 7/2009 | Ribault .................... C12Q 1/24 |
| | | 435/287.1 |
| 2010/0124563 A1 | 5/2010 | Coleman et al. |
| 2010/0233139 A1 | 9/2010 | Hedrick et al. |
| 2010/0279405 A1 | 11/2010 | Peterson et al. |
| 2011/0086426 A1 | 4/2011 | Freund |
| 2011/0206646 A1 | 8/2011 | Alfonso et al. |
| 2012/0255373 A1* | 10/2012 | Foster ............... B01L 3/502761 |
| | | 73/863.21 |

* cited by examiner

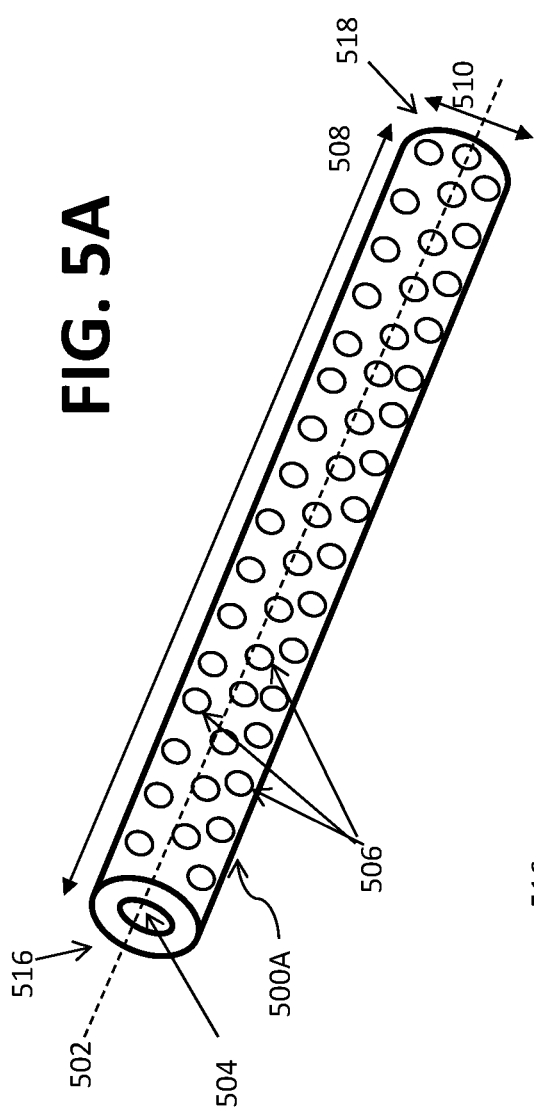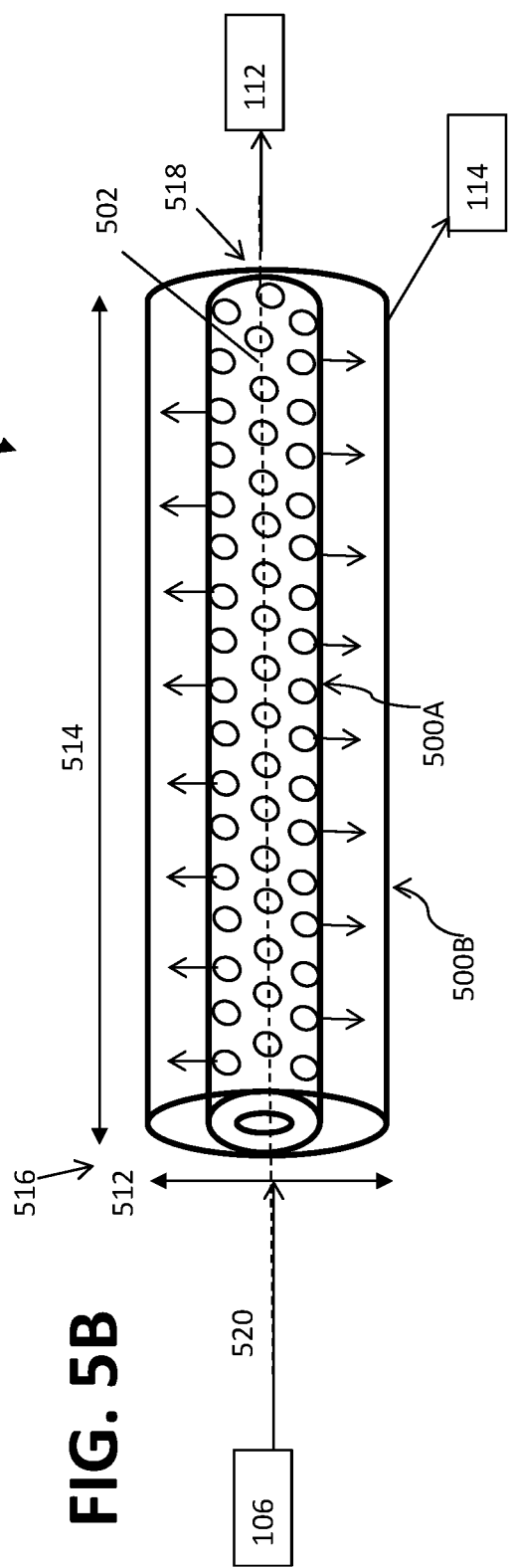

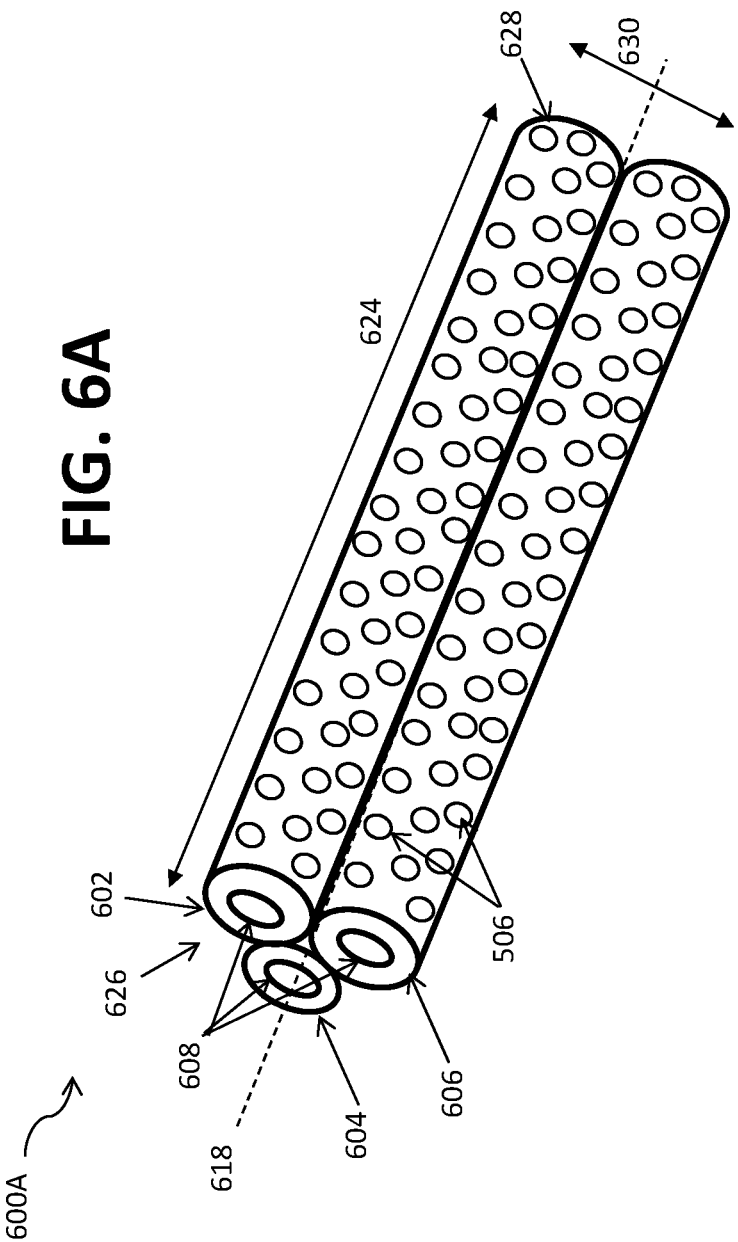

US 11,821,824 B2

CELL SEPARATION APPARATUS

CROSS-REFERENCE TO RELATED APPLICATIONS

This application is a continuation-in-part of and claims priority to U.S. patent application Ser. No. 14/221,272, filed Mar. 20, 2014, entitled "Hand-Held Adipose Processor and Cell Concentrator," which is a continuation-in-part of U.S. patent application Ser. No. 13/844,548 filed Mar. 15, 2013 entitled "Hand-Held Micro-Liposuction Adipose Harvester, Processor, and Cell Concentrator," which claims the benefit of and priority to U.S. Provisional Application Ser. No. 61/703,742, filed Sep. 20, 2012 and entitled "Hand-Held Micro-Liposuction Adipose Harvester, Processor, and Cell Concentrator," all of which are incorporated herein by reference in their entirety for all purposes.

BACKGROUND

Adipose tissue has numerous uses. When such tissue is digested, the freed cells are capable of a multitude of uses, including tissue engineering, tissue repair, release of therapeutic factors by the cell, including factors released as a result of genetic engineering of the cells.

SUMMARY

In an embodiment, a system for obtaining a target cell volume, comprising: a first chamber comprising a first separation mechanism and configured to separate a volume of biological material into a first retained volume and a first transfer volume; a second chamber in fluid communication with the first chamber and configured to: receive the first transfer volume from the first chamber and separate, in response to receiving the first transfer volume, a second transfer volume and a second retention volume from the first transfer volume. In an embodiment, the system further comprises a third chamber comprising a first side and a second side, wherein the first side is in fluid communication with the second chamber and configured to: receive the second transfer volume; and separate a third transfer volume and a waste volume from the second transfer volume; a pump in fluid communication with at least the third chamber, wherein the pump is configured in a first state to establish a horizontal flow of the second transfer volume from the first side of the third chamber to the second side of the third chamber; a waste collection repository in fluid communication with the second side of the third chamber via a first coupling and configured to receive the waste volume; and a product collection repository in fluid communication with the second side of the third chamber via a second coupling and configured to receive the third transfer volume, wherein the third transfer volume comprises a predetermined volume of cells and fluid.

In an embodiment, a method of obtaining a target cell volume, comprising: separating, via a first separation mechanism in a first chamber of a cell separation apparatus, and when a pump coupled to the cell separation apparatus is in an activated state, a starting volume of biological materials into a first transfer volume and a first retained volume; transferring the first transfer volume into a second chamber of the cell separation apparatus, wherein the second chamber is fluidly coupled to the second chamber; separating, via a second separation mechanism coupled to the second chamber, the first transfer volume into a second transfer volume and a second retained volume; transferring the second transfer volume into a third chamber of the cell separation apparatus, wherein the second chamber is fluidly coupled to the third chamber; separating, via a third separation mechanism coupled to the third chamber, the second transfer volume into a first cell volume, wherein separating the second transfer volume comprises performing at least one separation cycle; obtaining, subsequent to the at least one separation cycle, the first cell volume in the product collection repository.

In an alternate embodiment, a system for obtaining a target cell volume, comprising: a first chamber comprising a first separation mechanism, wherein the first separation mechanism is configured to separate a volume of biological material into a volume of fibrous tissue and lipids and a first transfer volume; a second chamber in fluid communication with the first chamber, wherein the second chamber comprises a second separation mechanism configured to receive the first transfer volume from the first chamber and separate out a second transfer volume; a third chamber in fluid communication with the second chamber; a waste repository in fluid communication with the third chamber; a product collection repository in fluid communication with the third chamber; and a pump, wherein the third chamber comprises a third separation mechanism configured to separate the second transfer volume into a cell volume comprising solids larger than a pore size of the third separation mechanism and a waste volume comprising solids smaller than the pore size of the third filter, and wherein the pump in a first activated state establishes a flow through the third chamber such that the cell volume is transferred to the product collection repository and the waste volume is transferred to the waste repository.

BRIEF DESCRIPTION OF THE DRAWINGS

For a detailed description of exemplary embodiments of the invention, reference will now be made to the accompanying drawings in which:

FIGS. 5A and 5B are schematic illustrations of a third separation mechanism and of the third separation mechanism disposed in the third chamber according to certain embodiments of the present disclosure.

FIGS. 6A and 6B are schematic illustrations of third separation mechanisms employed in the third chamber according to certain embodiments of the present disclosure.

NOTATION AND NOMENCLATURE

Figure 1:
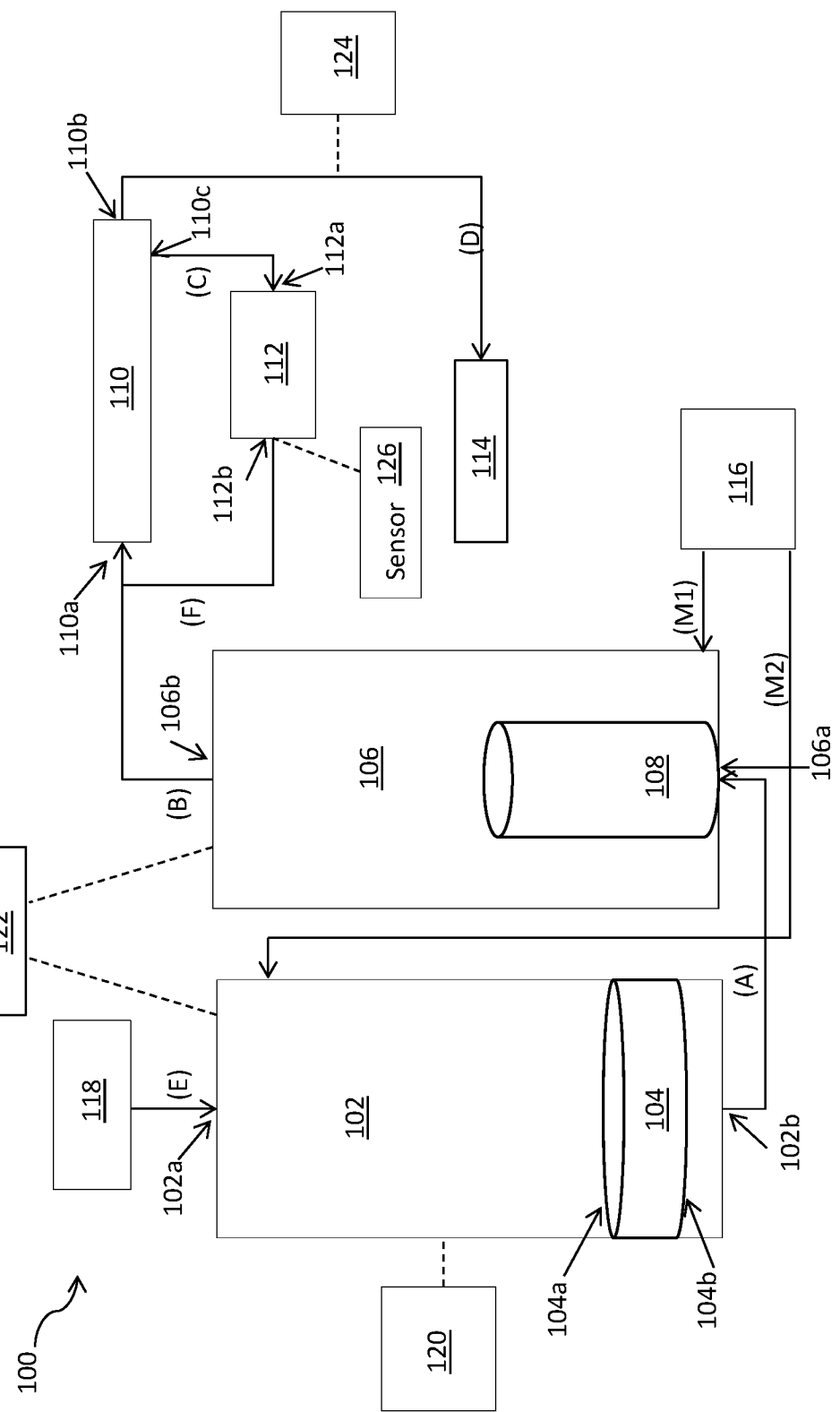
FIG. 1 is a schematic illustration of a system for separating a target cell volume according to certain embodiments of the present disclosure.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect, direct, optical or wireless electrical, physical (direct or magnetic) or fluidic connection. Thus, if a first device couples to a second device, that connection may be through a direct electrical connection, through an indirect electrical connection via other devices and connections, through an optical electrical connection, or through a wireless electrical connection.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

In the interest of clarity, not all of the routine features of the implementations described herein are shown and described. In the development of any such actual implementation, numerous implementation-specific decisions must be made in order to achieve the developer's specific goals, such as compliance with application, safety, regulatory, and business constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Existing methods of extracting and isolating adipose cells is that existing equipment, such as liposuction cannulas and pumps and digestion devices, are not expected to be very portable. Furthermore, the liposuction, digestion, and cell concentration are often carried out in separate devices, and there are consequent issues in maintaining sterility as tissue and cells are transferred between devices. Consequently, it would be advantageous to have a portable, sterile device which was capable of carrying out multiple functions, or all functions that produce harvestable cells, including extracting tissue, digesting the tissue, and concentrating the cells.

Described herein are embodiments of portable and partially or completely disposable (single-use) devices that isolate cells such as stromal vascular fraction (SVF) and stem cells from adipose tissue in order to obtain a target cell volume. The devices and systems herein may be referred to as a "cell separation apparatus," a term which may encompass a cartridge and/or a housing, casing, or body structure to which the cartridge may be coupled or removably coupled. As used herein, the term "cartridge" is used to describe a component that may be permanently or removably coupled into a body structure. Two components may be described as "removably coupled" when they may be de-coupled (separated) without rendering one or both components unusable, in contrast to permanent coupling where de-coupling the components renders both (all) unusable. It is to be appreciated that a target cell volume is different than a target cell count, and that the desired end result herein may be described in terms of target cell volume instead of target cell count since the cell count in a particular volume may vary among and between tissue samples and donors. A target cell count is the number or range of numbers of cells desired for harvest, whereas a target cell volume is a target volume of liquid that contains cells, but may not related directly to the number of cells in the volume. In contrast, a cell concentration is a measurement of a number of cells in a predetermined volume of liquid, for example, the number of cells in 1 mL of liquid. The concentration of cells in a volume of liquid may be increased by the systems and methods discussed herein, in particular in the third chamber where a liquid volume may be reduced by repeated filtering cycles.

In an embodiment, the system discussed herein may process, purify, and concentrate cell product. In one embodiment, it may also separate and harvest fat. Adipose tissue may, in one example, be processed in one continuous cycle. One embodiment is an integrated system that is miniaturized and may be hand-held. Use of the term "handheld" herein means a portable device that is capable of being held in one hand and, in some cases, operated using a single hand. In one example of use of the systems and methods discussed herein, a volume of adipose tissue harvested may be less than approximately 20 mL. Larger volumes of adipose tissue (e.g., 30 mL, 40 mL, 100 mL, etc.) may be also be accommodated by scaling the device. In one example, the device may accept aspirated adipose tissue into a cassette style configuration that comprises a series of connected chambers such as syringe bodies. These are sequentially, fluidly connected, chambers that may be arranged in various configurations as discussed herein. Each chamber may aid in digestion and processing of the adipose tissue, which may collectively enable the process to execute in a continuous and closed cycle, thereby reducing the sterility and safety concerns of previously employed systems.

Systems and methods discussed herein are directed towards separating cells from a sample comprising tissue, fluids, lipids, and other biological materials. The system discussed herein may be an entirely disposable system wherein a plurality of separation chambers, separation devices such as filters, motors, tubing, and other components are single-use components and are disposed of, not refurbished nor repaired, subsequent to a single use. As discussed herein, a "single use" of the device may comprise separating cells from a predetermined volume of biological material that is disposed in a digestion chamber.

In an embodiment, a plurality of separation chambers may be configured as to be fluidly connected to each other to form a cartridge. In some embodiments, the cartridge may be subsequently removed from the body structure and disposed, and in alternate embodiments, the body structure may also be disposable and the entire assembly may be disposed of after a single use. Various cartridges may be configured according to embodiments of the present disclosure, these configurations may include different combinations of chamber sizes, separation mechanism sizes, shapes, coupling mechanisms, and functionalities (e.g., pore sizes and direction of flow). In an embodiment, the systems and methods herein are directed towards an ordered combination of at least the separation mechanisms discussed herein that are configured to generate a target cell volume and/or target a cell population in the final product. For example, smaller filter pores in a dynamic wash chamber as discussed herein may lead to a higher concentration of cells that are more "stem-like" versus cells that are more "endothelial-like."

Larger pores in a separation mechanism in the dynamic wash chamber may be configured to lead to more equal populations of these two cell types.

Digestion Chamber

In an embodiment, the digestion chamber may comprise a syringe or syringe body, and an initial volume of biologic material may be disposed in the digestion chamber, for example, along with enzymes, to separate the lipids from the solid material. In some embodiments, prior to disposal in the digestion chamber, the biological material may be disposed in an apparatus such as a mincer to reduce the size of the solids in the sample. In that example, the minced product may be fed directly into the digestion chamber.

In an embodiment, the digestion chamber is configured such that a first separation mechanism such as a filter comprising a pore size of 50 microns to 200 microns is disposed at least part of the way in the chamber such that it takes up the entire inner diameter of the chamber and no material passes from a first side to a second side of the chamber without going through the first separation mechanism. In an embodiment, the first separation mechanism may be disposed at the 5 mL mark of a 60 mL syringe body that serves as the digestion chamber. This first separation mechanism separates lipid material and fibrous material from a plurality of cells, and the plurality of separated cells are transported to a second chamber. In some embodiments, a fluid comprising media and at least one type of digestive enzyme is pumped through the digestion chamber either a discrete number of times or continuously during the first separation process which occurs in the digestion chamber. In an embodiment, a pressure pump or other vessel may be associated with and/or coupled to the device to provide a supply gas, for example compressed air, oxygen or nitrogen, a vacuum pump may be employed and configured to provide negative pressure. This positive or negative pressure may be used to move fluids throughout the system.

In an embodiment, positive pressure may be induced through the use of an incorporated micro-pump or series of micro-pumps. In another embodiment, a pump in a base may pressurize a vessel in the hand-held while it is cradled in a base, so that the hand-held may operate independent of the base. In another embodiment, a pump in the base may supply positive pressure and negative pressure for the hand-held only while it is cradled, thereby only moving fluids by pressure during the cradled phase. Fluid flow may be managed by the cycling of valves, including check valves, electrically actuated valves, and other valves.

In an embodiment, the first separation mechanism acts to separate and trap a plurality of residual fibrous segments that remained undigested in the biological material, thereby also reducing the chances of down-stream clogs in the fluidics. This trapped volume may be subsequently removed and further processed. This first separation mechanism also ensures no particles greater than the pore size are contained in the first transfer volume. In some embodiments, the pore size of the first separation mechanism may be associated with a regulatory requirement in various countries (e.g., a maximum diameter or range of diameters for solids) for injectable media.

In some embodiments, an optic component may be coupled to or in communication with a portion of the digestion chamber. This optic component may be an optic sensor. The portion of the digestion chamber where the sensor is located may be located on a first side of the first separation mechanism in an area in between the first separation mechanism and the outflow point, or on a second side of the first separation mechanism in between the mechanism and the inflow/injection point. This optic sensor may be used to determine when the filtered sample comprises fluid and when that fluid changes to fat, such that only the fluid, and not the fat (lipids) are transferred with the first separated cell volume into the dynamic wash chamber. The optic sensor may be configured to activate a valve or to signal a durable or disposable pump that is in fluid communication with both the digestion chamber and the dynamic wash chamber. This optic sensor would thus be the trigger to cease pumping by closing the valve or deactivating the pump based on the determination.

Dynamic Wash Chamber

In an embodiment, the second chamber may be referred to as a dynamic wash chamber, and may comprise a second separation mechanism such as a filter. This second separation mechanism may be configured differently from that of the digestion filter in the digestion chamber. The first separation mechanism in the digestion chamber may be disposed at an end opposite to where the biological material is introduced to the chamber. In addition, it takes up the entire diameter of the chamber, and may not be in direct contact with the exit point of the digestion chamber. In contrast, the second separation mechanism is in direct contact with an entry point of the dynamic wash chamber such that the separated cells from the digestion chamber are introduced to the dynamic wash chamber and the first transfer volume enters the chamber via the second separation mechanism. The second separation mechanism may comprise an average pore size from about 5 microns to about 40 microns, in some embodiments a 10-micron pore size mesh may be used. The second separation mechanism traps an undesired plurality of particles from the first transfer volume and allows only the desired cell material to pass through the second separation mechanism and into the dynamic wash chamber to form a second transfer volume. In an alternate embodiment, the second chamber does not comprise the second separation mechanism and is used as a dynamic wash chamber to dilute the enzyme but not as a separation chamber.

In an embodiment, the second separation mechanism may be configured as a cylindrical device coupled to the entry port of the dynamic wash chamber, such that the second separation is aligned with the entry port along a common center axis. In an embodiment, outer diameter of the second separation mechanism is from 20% to 80% the size of the inner diameter of the dynamic wash chamber. In some embodiments, the dynamic wash chamber may be configured such that media is circulated through the dynamic wash chamber on a continuous basis when the separated material from the digestion chamber is introduced into the dynamic wash chamber. The second separated cell volume is created via the dynamic wash chamber and comprises fluid and a plurality of cells that are smaller than the pore size of the second separation mechanism or pliable such that the cells are able to be compressed and fit through the pores despite having an at least one measurement that is greater than the pore size. Thus, the dynamic wash chamber is used to dilute and clean the first volume of separated cells received from the digestion chamber by retaining the larger-sized particles within the second separation mechanism and allowing the desired plurality of cells to pass through it and form the second transfer volume.

Horizontal Flow Chamber

The second transfer volume may be transferred to a third chamber comprising a third separation mechanism. The third chamber may have a first side where the second transfer volume enters and a second side where a filtered volume is transferred to waste and a retained volume is transferred to the product collection repository. A substantially horizontal flow is established from the first side to the second side, such that the second transfer volume enters the third chamber via the third separation mechanism. This process may be completed in a single cycle to obtain the target cell volume, or may be performed in multiple separation cycles, where each subsequent cycle produces a smaller volume of retained volume and a higher concentration of cells, since more fluid and solids are filtered out with each subsequent cycle.

In an embodiment, a system 100 as shown in FIG. 1 may be configured to separate and collect cells from a lipid-based sample. As shown in FIG. 1 in the system 100, which may be alternatively referred to as a device 100, a volume of biological material may be disposed in a digestion chamber 102 via a path (E). The digestion chamber 102 may operate at an elevated temperature as compared to room temperature, and may comprise a first side 102a and a second side 102b. A heating mechanism (not pictured) may cause the digestion chamber, and thus the materials disposed within, to be maintained at a temperature from about 32° C. to about 40° C. while the device 100 is in use.

In some embodiments, a mincer 118 or other mechanism configured to reduce an average size of tissue may be used prior to disposal of the volume of biological material in the digestion chamber 102. The first side 102a may comprise an entry port that may also be referenced as 102a, this entry port 102a may be a part of the path (E). This mechanism 118 may be used to further reduce the size of fibrous material in the volume of biological material in order to increase the efficiency of the system 100. Enzymes and other materials may also be introduced through the entry port 102a. In an embodiment, the volume of biological material introduced at (E) is pushed through the chamber 102 from the entry port 102a to a second side 102b that may also be referred to as the exit port 102b. It is understood that the chambers discussed herein may comprise syringe bodies or other containers, as appropriate. The initial volume introduced at (E) passes through a first separation mechanism 104 that may be referred to as a digestion filter 104. In an embodiment, the digestion filter 104 may be configured to separate a first plurality of solids and a lipid volume from the volume of the sample introduced at (E). The digestion filter 104 may comprise a first side 104a and a second side, such that a first volume of separated cells (herein referred to as the "first transfer volume") is captured after being passed through the filter 104 on the second side 104b. The first transfer volume may be transferred via an outflow point, exit port 102b, of the digestion chamber 102 via a path (A), and transferred into the dynamic wash chamber 106.

The dynamic wash chamber 106 may comprise a first side 106a and a second side 106b, the first side 106a may comprise and thus be referred to as an entry port 106a. Similarly, the second side 106b may comprise and be referred to as an exit port 106b. An electromechanical element 122 may be employed in the system 100, this device 122 such as a pump may provide pressure, suction, or a vacuum that may be self-powered and used to drive the process, e.g., to automate the cell separation and extraction product, and also to preserve extracted cells collected in a product collection vessel/repository 112 for an extended period of time prior to harvesting (removal from the system 100). The device 122 may act in conjunction with a valve 124 which may act as a pinch-off mechanism to control the back pressure of upstream filters during the separation process(es).

In an embodiment, a sensor 120 such as an optic sensor is coupled to the digestion chamber 102. This sensor 120 may be located between the first separation mechanism 104 in a region in between the first separation mechanism 104 and the outflow point 102a. In another embodiment, the sensor 120 may be located in a region created between the first side 102a of the mechanism 104 of in between the mechanism and the inflow/injection point indicated by the path (E). This optic sensor 120 may be configured to determine when at least one optic property of the volume in the chamber 102 is lipid, not fluid, and may signal a durable or disposable pump or valve in fluid communication with both the digestion chamber and the dynamic wash chamber to cease pumping or flowing based on this determination so that lipids are not passed into the fluidics of the system 100, as that may clog the system 100 and render it unusable and/or less effective. In an embodiment, media from a media reservoir 116 may be pumped into the digestion chamber 102 via a path (M2) during the first separation process in the chamber 102. The media reservoir 116 may comprise water for injection (WFI), lactated ringers, or Harman's solution.

The dynamic wash chamber 106 may be configured such that a second separation mechanism 108 may be disposed within the dynamic wash chamber 106 as to be in fluid communication with the path (A). When the first transfer volume is introduced to the chamber 106, it is introduced via the second separation mechanism 108 such that none of the first transfer volume enters the chamber 106 without passing through the mechanism 108. Thus, in contrast to the digestion chamber where biological material flows through the chamber 102 and is separated into the first cell volume after being passed through the filter 104, the first volume of separated cells transmitted along the path (A) first enters the dynamic wash chamber via the filter 108, such that only second volume of separated cells enters the chamber 106. The second separation mechanism 108 may comprise an average pore size from about 1 micron to about 40 microns. In some embodiments, a continuous flow of media from the media reservoir 116 may be pumped through the chamber 106 during this process via a path (M1). Depending upon the embodiment, the second separation mechanism 108 may extend from 15%-80% of a length of the dynamic wash chamber 106, and may comprise a width from about 20% to about 80% of an inner diameter of the chamber 106, and is centered so that it does not abut or contact the inner walls of the chamber 106. In alternate embodiments, the second separation mechanism 108 may have a width that is the same as or substantially similar to the inner diameter of the chamber 106.

In an embodiment, the second transfer volume is separated via the second separation mechanism 108. That is, the second transfer volume separated via the second separation mechanism 108 flows along a path (B) to a third chamber 110 such that the second transfer volume exits the second chamber 106 via the port 106b. It is appreciated that the fluid volume transfers and media circulations discussed herein are accomplished via a series of tubes and connectors that may be arranged in various configurations depending upon the size/shape and other properties of the other components in the system 100. The third chamber comprises a first side 110a and a second side 110b as well as a third separation mechanism, not shown in FIG. 1 but illustrated in FIGS. 5A, 5B, 6A, and 6B. This third separation mechanism may comprise one or more fibrous filters of varying sizes that extend horizontally along a horizontal flow path through the third separation mechanism in the third chamber 110 from the first side 110a to the second side 110b of the chamber 110. The third separation mechanism may be coupled to one or both ends (110a and 110b) of the chamber, which may be referred to herein as entry 110a and exit ports 110b.

The third separation mechanism may comprise a hollow fiber filter comprising multiple fibers arranged parallel to each other and to a direction of fluid flow. The plurality of hollow fibers may comprise sub-micron pore sizes, e.g., pore sizes from 0.005-0.99 microns. In another embodiment, the third separation mechanism may comprise a design that operates in a similar way to the second separation mechanism 108, such that the volume retained by the third separation mechanism, the "hold-up volume," is at least the desired finished product volume.

In an embodiment, a flow is established horizontally through the third chamber 110 from the first side 110a to the second side 110b such that, in a first separation cycle, a volume transferred along (B) is separated in the third chamber 110. During this separation in the third chamber 110, a portion of the volume transferred from the second chamber 106 to the third chamber 110 along (B) passes through the separation mechanism and into a waste repository 114 via the exit port 110b (waste port) along (D). A second portion of the volume transferred from 106 to 110 via (B) is captured by the third separation mechanism in the third chamber 110 during the separation. This may be a harvestable cell volume and may be and transferred via the exit port 110b along the path (C) to a product collection repository 112. The passage of a volume of biologic material through the first, second, and third chambers such that each chamber is used once to obtain a desired target cell volume and/or population in the product collection repository, which may be referred to as a "single separation cycle."

In some examples, additional separation cycles may be performed using one or more chambers. In one example, a single separation cycle may be used in the third separation mechanism in order to obtain a desired target cell volume in the repository 112. In alternate embodiments, a plurality of separation cycles may be performed using one or more chambers such that the cell volume in the volume transferred to the product collection repository becomes more concentrated (e.g., more cells, less fluid) with each cycle.

In one example, the repository 112 may be coupled to or otherwise in communication with a sensor 126 such as a level or a pressure sensor 126. In this example, the separation process is automated such that manually or automatically disposing a biological volume in the mincer 118 or in the digestion chamber 102 begins the separation process to obtain the desired cell volume in the repository 112. In this example, subsequent to the first separation cycle discussed above where the volume transferred from the chamber 106 along (B) to the third chamber 110 is separated after a first run through the third separation mechanism 110, the volume transferred to the repository (112) via the path (C) and a second exit port 110c is recirculated through the third chamber 110 (and thus the third separation mechanism) along path (F). Thus, a different, lesser volume than the start volume of this subsequent cycle is transferred into the product collection repository 112. During this subsequent cycle, an additional volume is also transferred to the waste repository 114 along the path (D) via the exit port 110b.

The product cell repository 112 volume may be dynamically cycled and separated via the third separation mechanism in the third chamber 110 for a plurality of cycles in this manner until the sensor 126 determines that the target volume has been obtained. Stated differently, an initial cell volume separated by the sequential first, second, and third separation operations in each of the chambers 102, 106, and 110, may be further separated via subsequent cycles using at least the third separation mechanism to obtain a target cell volume in the repository 112. The subsequent separation steps remove fluid and solids that are smaller than the pore size of the third separation mechanism 110. Thus, the second chamber 106 increases the transfer volume from 102 by diluting the residual enzyme used in the first chamber 102. The third chamber 110 subsequently concentrates (e.g., removes liquid while preserving target cells) the transfer volume from the second chamber 106 by separating out volumes comprising the residual enzyme. That is, a first volume transferred to the repository 112 via the path (C) may comprise X, X is cycled through the third chamber 110 to form a second volume transferred to the repository 112 that may comprise X-Y, which is less than X. In one example, the second transfer volume (X-Y) may be cycled along a path (F) back through the third separation mechanism for a third time to form a third volume in the repository of (X-Y)-Z, which is less than the second volume (X-Y). In this example, the third volume is less than the second volume, which is less than the first volume. In one example, when the sensor 126 determines that the target cell volume has been reached, the electromechanical elements that may comprise pumps, such as 122 and 124, are shut off. Subsequently, the target cell volume collected in the repository 112 is extracted (harvested), and the entire device 100 is disposed such that components cannot and are not reused. In some examples, the target cell volume collected in the repository 112 is maintained in the repository 112 for a predetermined time and may be agitated, heated, or cooled prior to being harvested from the repository 112.

In an alternate example, the sensor 126 may not be employed and, instead, the volume transferred along the path (C) from the second exit port 110c to an entry port 112a of the repository 112 exits the repository 112 via an exit port 112b. An at least one interior surface of the repository 112 may be curved such that the volume present settles, and, when a target cell volume is reached, the volume sits below the exit port 112b such that suction or other pressure/pumping of the volume out through the exit port 112b is not possible since the cell volume present in the repository is seated below the level of the exit port 112b. Thus, activity caused by the pumps/valves 122/124 to attempt to transfer volume along (F) therefore only draw air and not biologic material, thus ending the separation cycle or plurality of separation cycles. As shown herein, the system 100 in FIG. 1 may be disposable and referred to as a cartridge, and may be removably coupled to a cartridge housing. The disposable cartridge is removed from the cartridge housing after the cells are harvested from the repository 112. In alternate embodiments, the cartridge may be coupled to the housing such that the cells can be removed from the repository 112 without disassembly and the entire assembly (cartridge and housing) is disposed.

Figure 2:
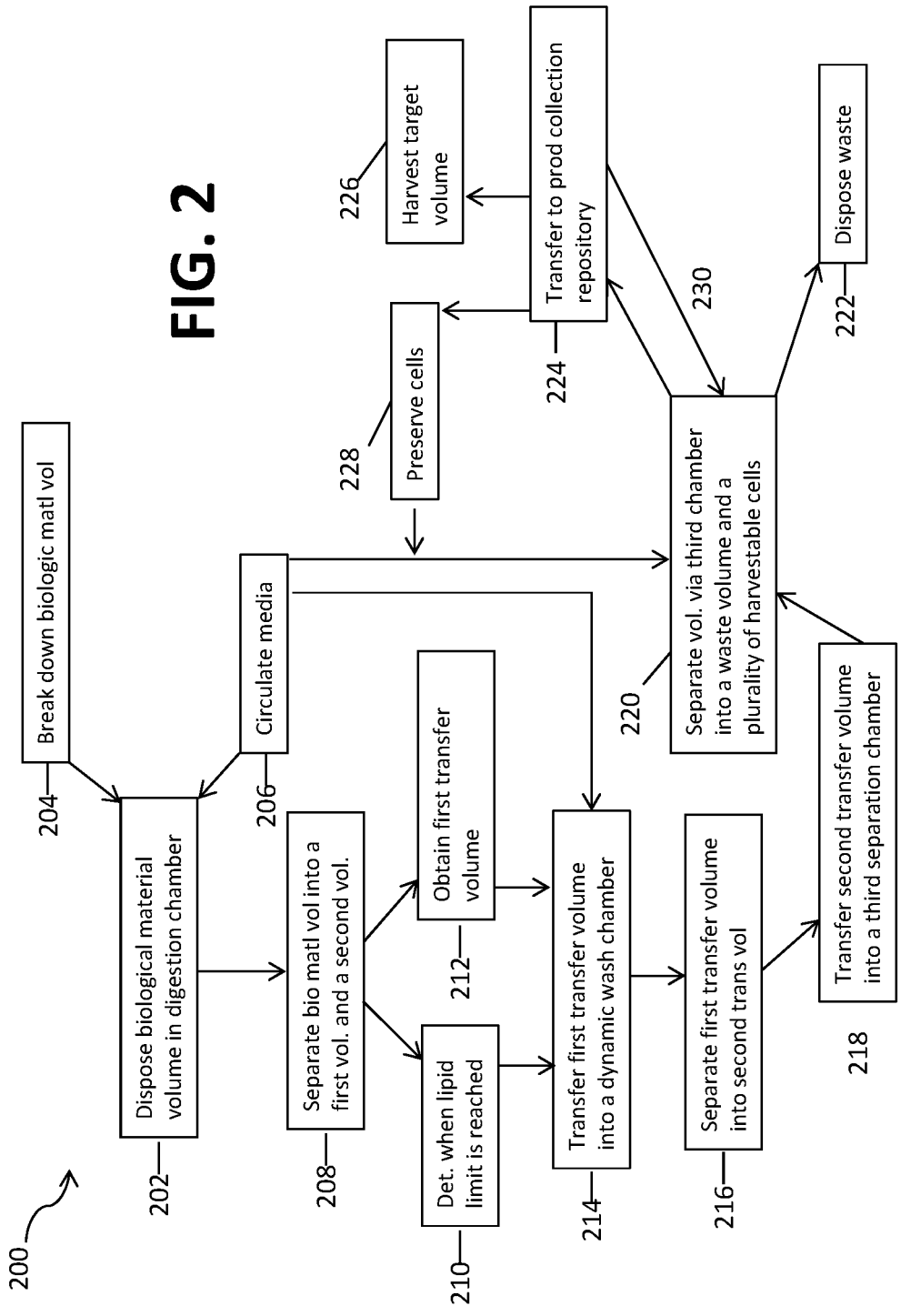
FIG. 2 is a flow chart of a method of separating a target cell volume according to certain embodiments of the present disclosure.

FIG. 2 is a flow chart of a method 200 of separating a desired cell volume from a volume of biological material. In the method 200, at block 202, a volume of biological material may be disposed in a first chamber that may be referred to as a digestion chamber. This volume of biological material disposed at block 202 comprises fibrous tissue, lipid content, and cells to be separated, this cell volume may be referred to as the "desired" or "harvested" cell volume. The digestion chamber may comprise a syringe or syringe body, for example, a 35 mL, 60 mL, 120 mL, or other size syringe body as appropriate for the desired cell volume. The digestion chamber may be heated to from about 35° C. to about 40° C. prior to disposal of the volume and during the separation process. The digestion chamber comprises a first separation mechanism disposed at an end of the syringe opposite an entry port. That is, the first separation mechanism is disposed towards the exit port of the digestion chamber such that the biological volume of material is passed through the digestion chamber to form a first (transfer) volume to transfer to another chamber and a second (retained) volume. The first separation mechanism may comprise an average pore size such as 200 microns, and may be coupled to the digestion chamber as to not allow any of the biological material to flow around it, rather, any material disposed in the digestion chamber is to be passed through the first separation mechanism in order to separate out a plurality of fibrous material and solids that are larger than the pore size of the first separation mechanism, as well as lipids, from the first transfer volume. In some embodiments, at block 204, prior to the disposal of the biological material volume in the digestion chamber, some or all of the volume may be further broken down, for example, using a mincer.

In an embodiment, at block 206, media such as digestion enzymes may be circulated through the digestion chamber to aid the process. At block 208, the volume of biological material is separated into the first transfer volume and the second retained volume, the first transfer volume is obtained at block 212 when the separation at block 208 is complete. In an embodiment, the first separation process in the digestion chamber may be determined to be complete and thus terminated at block 210, for example, when an optic sensor determines that the composition in the digestion chamber has reached a predetermined lipid level. When an optic sensor is employed in the digestion chamber or in other parts of the system discussed herein, the chamber or other component that the optic sensor(s) is coupled to is sufficiently clear as to enable the optic sensor to perform this analysis.

At block 214, the first transfer volume is transferred into the dynamic wash chamber. As discussed herein, the transfer of various volumes among and between components may be accomplished via a series of flexible and/or rigid tubing that is configured to allow fluid communication between components. These transfers may be promoted, triggered, or otherwise aided by one or more pumps and valves that create positive pressure and/or suction at various points in the process. It is to be appreciated that media may be circulated at block 206 through the dynamic wash chamber during the receipt of the first transfer volume and/or subsequently. When the first transfer volume is transferred into the dynamic wash chamber at block 214, it may be transferred via a second separation mechanism coupled to an entry port of the dynamic wash chamber, such that introducing the first transfer volume at block 214 separates the first transfer volume into a second transfer volume at block 216. The second separation mechanism may comprise a pore size smaller than that of the first separation mechanism, such that the second transfer volume formed at block 216 comprises an average particle size of less than those of the first transfer volume.

In an embodiment, at block 218, the second transfer volume is transferred to a third separation chamber that comprises a third separation mechanism. The third separation mechanism may be configured such that a plurality of hollow tube filters with porous walls are parallel to a horizontal flow that is established by the transfer of the second transfer volume to the third chamber. This third separation mechanism comprises a plurality of pores that are smaller than those of the first and second separation mechanisms, and is configured to separate a waste volume from a harvestable cell volume at block 220. This separation at block 220 includes transferring the waste volume and harvestable cell volumes to separate repositories.

The waste volume is disposed at block 222 in a waste repository, and a harvestable volume of cells is transferred to a production collection repository at block 224 and may be harvested at block 226. The harvesting at block 226 comprises removing some or all of the product transferred to the product collection repository at block 224. The separation at block 220 may comprise moving the second transfer volume from an entry port to an exit port of the third chamber. The second volume moves through the porous tube or tubes of the third separation mechanism and the waste volume, which comprises liquid and solids smaller than the cells of the target cell volume, is filtered out radially and/or horizontally and transferred to the waste repository. In an embodiment, the harvestable volume separated at block 220 may be separated during a single separation cycle comprising transferring the second transfer volume through the third chamber once, and harvesting the target volume at block 226. In some embodiments, the remainder of material in the digestion chamber left after the separation at block 208 and/or the volume disposed in the waste repository at block 222 may be harvested as well.

In an alternate embodiment, the harvestable volume separated at block 220 may be separated during a plurality of separation cycles comprising transferring the second transfer volume through the third chamber, separating the harvestable cell volume, transferring it to the product collection repository, and then re-circulating the separated harvestable cell volume along a path 230. The re-circulated volume is re-filtered through the third chamber at block 220, and the re-circulated volume is thus further separated into a smaller harvestable cell volume than what was obtained during the first cycle. Subsequent separation cycles may be performed until the target cell volume is detected as being present in the product collection repository and harvested at block 226.

Figure 3:
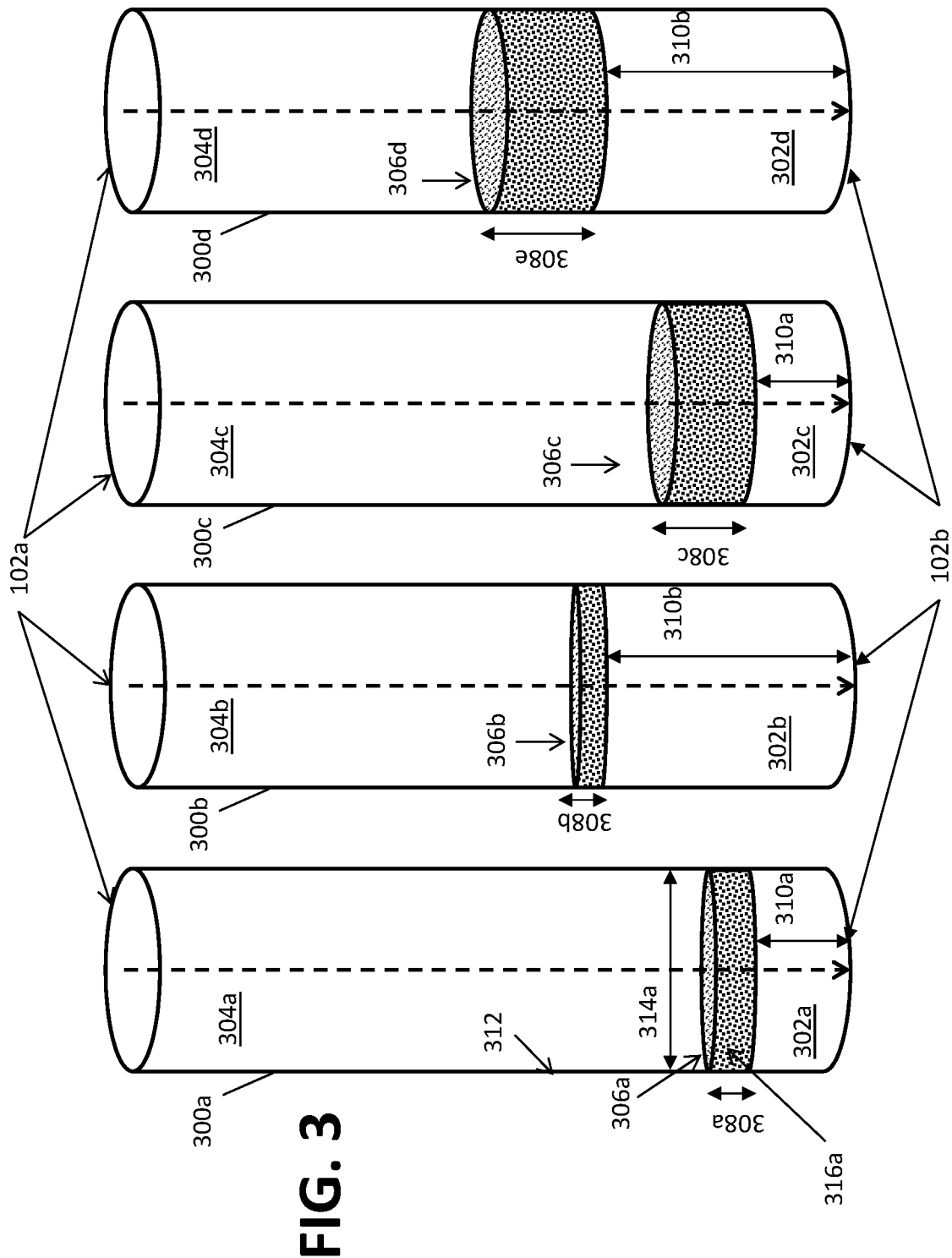
FIG. 3 is a series of partial schematic illustrations of digestion chambers comprising separations mechanisms in various configurations according to certain embodiments of the present disclosure.

FIG. 3 is a series of partial schematic illustrations of digestion chambers 300a-300d comprising separations mechanisms 306a-306d in various configurations. It is to be appreciated that the dotted-line arrows indicate the direction of fluid flow through the digestion chambers 300a-300d. FIG. 3 illustrates the first side 102a and the second side 102b of each digestion chamber 300a-300d, it is to be appreciated that these examples are provided to illustrate examples of sizes and positions of separation mechanisms 306a-306d. In the first digestion chamber 300a, the first separation mechanism 306a comprises a thickness 308a that may be, for example, equivalent to 5 mL in the chamber 300a body. The first separation mechanism 306a is located a distance of 310a from the second side 102b of the first digestion chamber 300a. Thus, the separation of the biological material volume discussed herein that employs the digestion chamber 300a results in a lipid and solid volume being retained in a retention portion 304a of the first digestion chamber 300a, and a transfer volume is retained in a transfer/collection portion 302a of the second digestion chamber 300b. The separation mechanism 306a is secured to the inner surface 312 of the chamber 300a such that a diameter 314a of the mechanism 306a is configured to create a press-fit seal with the inner surface 312 of the chamber 300a such that there is no fluid flow (fluid is prevented from flowing) between the outer diameter of the separation mechanism 306a and the inner surface 312 of the chamber 300a. It is to be understood that the outer diameter of the mechanism 306a is a surface 316a of the diameter 314a.

Chambers 300*b*, 300*c*, and 300*d* are configured similarly such that fluid flowing in the direction of the dotted arrows is prevented from flowing around the separation mechanisms 306*b*, 306*c*, and 306*d*, and instead flow through the separation mechanisms 306*b*, 306*c*, and 306*d* to generate the respective transfer volumes discussed herein. The second (300*b*), third (300*c*) and fourth (300*d*) digestion chambers shown in FIG. 3 each comprise similar features to that of the first digestion chamber 300*a*, except that the size and/or position of the separation mechanisms 306*b* and 306*d* is different from that of 306*a* and 306*c*. With respect to size (thickness) of the separation mechanisms 306*b* and 306*d*, the respective thicknesses 308*c* and 308*d* are greater than those of the separation mechanisms 308*a* and 308*b*. In an embodiment, the respective thicknesses 308*c* and 308*d* may comprise thicknesses that correspond, for example, to 10 mL or 15 mL of the chamber (306*a* and 308*a*) bodies. In addition, the pore sizes (not shown here as differing) may differ among and between embodiments, such that the pore size of the separation mechanisms 306*a*-306*d* may be from about 50 μm to about 200 μm. Turning to the position of the separation mechanisms, the position of the separation mechanisms 306*b* and 306*d* are located at a distance 310*b* such that the retention portions 304*b* and 304*d* comprise larger volumes than the same portions 304*a* and 304*c*. In various embodiments, the retention portions 304*a*-304*d* may vary in volume from less than 10% of the overall volume of the chambers 300*a*-300*d* to about 50% of the overall volume, wherein the overall volume of each chamber is defined by the mL capacity, e.g., a distance from the first side 102*a* to the second side 102*b*. As illustrated in FIG. 3, and discussed herein, the separation mechanisms 306*a*-306*d* are disposed in each respective chamber 300*a*-300*d* as to span the entire inner diameter of each chamber, otherwise the separation mechanisms would not be functional as illustrated since biologic material would be able to flow freely around the separation mechanisms 306*a*-306*d*.

Figure 4:
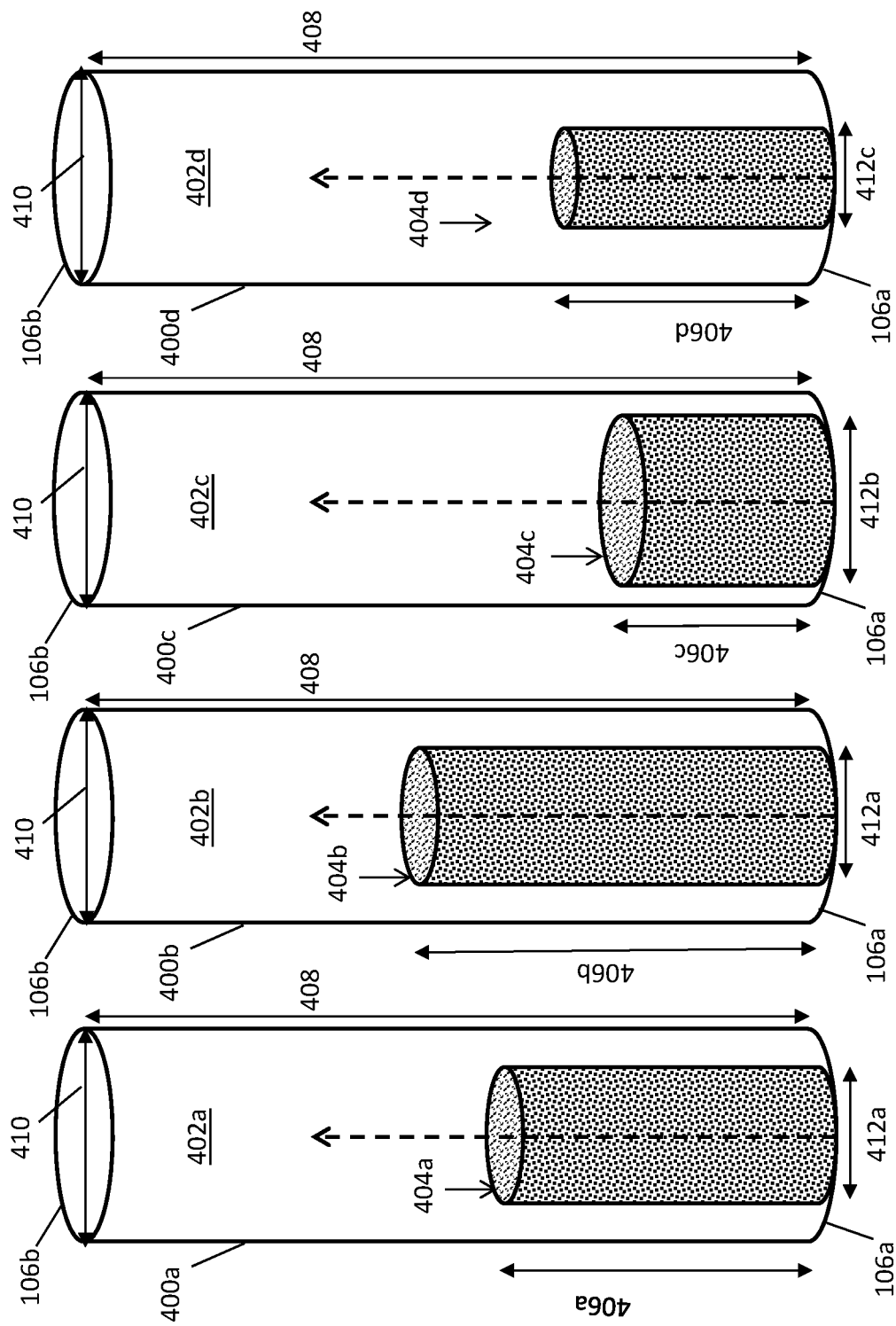
FIG. 4 is a series of partial schematic illustrations of dynamic wash chambers comprising separations mechanisms in various configurations according to certain embodiments of the present disclosure.

FIG. 4 is a series of partial schematic illustrations of dynamic wash chambers 400*a*-400*d* comprising separation mechanisms 404*a*-404*d* in various configurations. FIG. 4 illustrates the first side 106*a* and the second side 106*b* of each digestion chamber 400*a*-400*d*, it is to be appreciated that these examples are provided to illustrate examples of sizes and positions of separation mechanisms 404*a*-404*d*. A first chamber 400*a* comprises a first separation mechanism 404*a* with a length 406*a* that is less than an overall length 408 of the chamber 400*a*. The first separation mechanism 404*a* further comprises a width 412*a* that is less than the overall width 410 of the chamber 400*a*, such that the first separation mechanism 404*a* is not in contact with the sides of the chamber 400*a*, in contrast with the separation mechanisms 306*a*-306*d* in FIG. 3 which are secured to each chamber 300*a*-300*d* via a press-fit or similar sealing coupling to the inner surface 312. The first chamber 400*a* comprises a portion 402*a* that collects a transfer volume of fluid and solids, this portion is couple to an exit port (not shown) on the second side 106*b* and discussed above.

Chambers 400*b*, 400*c*, and 400*d* are configured similarly such that fluid flowing in the direction of the dotted arrows separated by the separation mechanisms 404*b*, 404*c*, and 404*d*, such that a retention portion (volume) of the fluid separated is retained in each separation mechanism 404*b*, 404*c*, and 404*d*, and a transfer portion (volume) is retained in the portions 402*b*, 402*c*, and 402*d*. The second (400*b*), third (400*c*) and fourth (400*d*) digestion chambers shown in FIG. 4 each comprise similar features to that of the first digestion chamber 400*a*, except that the length 406*b* of the second chamber 400*b* is greater than the lengths 404*a*, 404*c* (in the third chamber 400*c*), and 404*d* (in the fourth chamber 400*d*). The separation mechanisms may differ in, length as discussed above, or width, and/or porosity, as shown in 400*c* and 400*d* with respect to width. While the separation mechanisms 404*a* and 404*b* comprise the width 412*a*, which is greater than the width 412*c* of the fourth chamber 400*d* but less than the width 412*b* of the mechanism 404*c* in the third chamber 400*c*. Turning to the position of the separation mechanisms in FIG. 4, each separation mechanism 404*a*, 404*b*, 404*c*, and 404*d* is removably coupled to the first side 106*a* of each chamber 400*a*-400*d* such that the transfer volume of fluid to each chamber 400*a*-400*d* passes through each separation mechanism 404*a*-404*d* and only the separated volume that passes through each separation mechanism enters into the chamber portions 402*a*-402*d*.

FIGS. 5A and 5B are schematic illustrations of a third separation mechanism 500A and of the third separation mechanism 500A disposed in the third chamber 500B. In FIG. 5A, the third separation mechanism 500A comprises a through-hole 504 that is aligned a central axis 502 of the third separation mechanism 500A, the through-hole extends from a first side 516 to a second side 518 of the mechanism 500A. The third separation mechanism 500A also comprises an overall length 508 extending from the first side 516 to the second side 518 of the mechanism 500A, an outside diameter (OD) 510, and a plurality of pores 506. In an embodiment, the overall length 508 may be from 10 cm to 50 cm and the outside diameter 510 may be from 0.5 cm to 10 cm. While the plurality of pores 506 are shown in FIGS. 5A and 5B as being approximately round and of approximately equivalent size, in various embodiments the size, shape, and placement of the pores 506 may vary. In various embodiments, the total surface area (including the area created by the pores) of the third separation mechanism 500A may be from about 5 $cm^2$ to about 100 $cm^2$, and the average diameter of the plurality of pores 506 may be from about 0.2 microns to about 0.7 microns.

FIG. 5B illustrates the third separation mechanism 500A coupled to the third chamber 500B. The chamber 500B comprises an overall length 514 extending from the first 516 and second 518 sides shared with the mechanism 500A. The second chamber 106, waste repository 114, and product collection repository 112 are also illustrated. The third separation mechanism 500A is coupled to the third chamber 500B via the first 516 and second 518 sides of the mechanism 500A and is aligned with the central axis 502 shared by the chamber 500B and the mechanism 500A, such that the mechanism 500A is flush on both sides 516 and 518 with the chamber 500B so that when the fluid volume 520 is transferred from the second chamber 106, it is introduced to the third chamber 500B via the through-hole 504. When the fluid volume 520 enters the mechanism 500A, a plurality of solids smaller than a diameter or an average diameter of the plurality of pores 506, along with a portion of liquid transferred in the volume from the second chamber 106, is forced out of the volume and transferred into the waste repository 114 and a plurality of solids larger than the diameter or average diameter of the plurality of pores 506 is passed through the mechanism 500A to the second side 518 and transferred to the product collection repository 112.

In an embodiment, the volume transferred to the product collection repository 112 may be re-filtered through the chamber 500B, and, with each subsequent filtration cycle through the chamber 500B, the volume of liquid is decreased and the concentration of the cells increases. In one example, a first separation cycle via the third separation mechanism 500A may remove a first percentage of the fluid and cell volume, reducing the volume transferred to the product collection repository 112 by X %. X may be 10%, 20%, 30%, or other percentages based upon the configuration of the chamber 500B, e.g., the dimensions of the mechanism 500A and chamber 500B. The volume transferred to the product collection repository 112 after this first cycle may then be re-cycled through the chamber 500B to further reduce the volume of the sample by 10%, 20%, 30%, and so on, until a desired volume and/or concentration is transferred to the product collection repository 112.

Figure 6B:
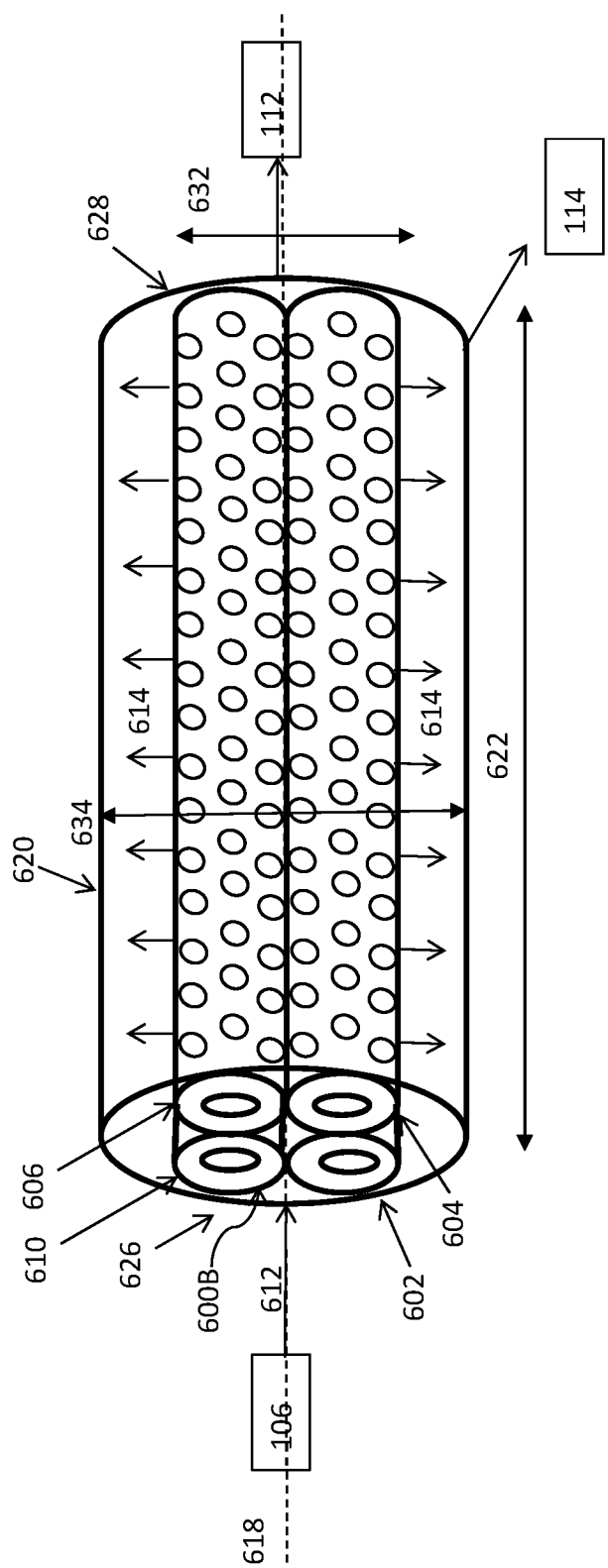

FIGS. 5A and 5B are an example of a third chamber 500B with a single separation mechanism 500A disposed therein. In alternate embodiments, for example, as shown in FIGS. 6A and 6B, multiple separation mechanisms 602, 604, and 606, may be employed in the third chamber. The example third separation mechanism assembly 600A shown in FIG. 6A is further defined by a central axis 618, an overall width 630, and an overall length 624, wherein each of the mechanisms 602, 604, and 606 are of a substantially similar length 624. A width (not shown) of each of the separation mechanisms 602, 604, and 606 may be substantially similar, or may be different, depending upon the embodiment. The three example separation mechanisms 602, 604, and 606 are shown as being positioned such that each is positioned at an equal distance from the other two along the central axis 618. Each of the separation mechanisms 602, 604, and 606 has a through-hole 608 extending from a first side 626 to a second side 628 of the assembly 600A and a plurality of pores 506. Each of the separation mechanisms 602, 604, and 606 may have varying sizes and shapes depending upon the embodiment.

FIG. 6B illustrates a third separation mechanism assembly 600B coupled to the third chamber 620. The chamber 620 comprises an overall length 622 extending from the first 626 and second 628 sides shared with the third separation mechanism 600B. The chamber 620 further comprises an inside diameter 634 and the separation mechanism assembly 600B comprises an outside diameter 632. The second chamber 106, waste repository 114, and product collection repository 112 from FIG. 1 are also illustrated. The third separation mechanism assembly 600B is coupled to the third chamber 620 via the first 626 and second 628 sides of the mechanism assembly 600B and is aligned with the central axis 618 shared by the chamber 620 and the mechanism assembly 600B. When coupled to the chamber 620, the mechanism assembly 600B is flush on both sides 626 and 628 with each side (626, 628) of the chamber 600B such that when the second fluid transfer volume is moved to the third chamber 620 from the second chamber 106, it introduced to the third chamber 620 via the assembly 600B. That is, none of the second transfer volume from the second chamber 112 enters the chamber 620 unless it passes through the separation mechanism assembly 600B. A horizontal flow 612 is established from the first side 626 to the second side 628. When the horizontal fluid flow 612 enters the mechanism assembly 600B, a plurality of solids smaller than a diameter or an average diameter the plurality of pores 506, along with a portion of liquid transferred in the volume from the second chamber 106, flow to outside of the assembly 600B as shown by arrows 614 and into a and transferred into the waste repository 114 and a plurality of solids larger than the diameter or average diameter of the plurality of pores 506 is passed through the mechanism assembly 600B to the second side 628 and transferred to the product collection repository 112.

In an embodiment, the volume transferred to the product collection repository 112 may be re-filtered through the chamber 620, and, with each subsequent filtration cycle through the chamber 620, the volume of liquid is decreased and the concentration of the cells increases. In one example, a first separation cycle via the third separation mechanism 600B may remove a first percentage of the fluid and cell volume, reducing the volume transferred to the product collection repository 112 by X %. X may be 10%, 20%, 30%, or other percentages based upon the configuration of the chamber 620, e.g., the dimensions of the mechanism assembly 600B. The volume transferred to the product collection repository 112 after this first cycle may then be re-cycled through the chamber 500B and/or the third mechanism 600B to further reduce the volume of the sample by 10%, 20%, 30%, and so on, until a desired volume and/or concentration (e.g., as determined by a sensor as discussed herein) is transferred to the product collection repository 112 for harvesting.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable expressed as a percent, for example, a weight or volume percent ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A system for obtaining a target cell volume, comprising:
   a first chamber comprising an inner diameter and a first separation mechanism, said first separation mechanism is configured to separate a volume of biological material into a first retained volume and a first transfer volume, said first separation mechanism is disposed in the first chamber to span said inner diameter so that all of said volume of biological material flows through said first separation mechanism and not around said first separation mechanism;

a second chamber comprising a length, a width, an inner surface and a second separation mechanism, said second chamber is in fluid communication with the first chamber and configured to:
  receive the first transfer volume from the first chamber and
  separate, in response to receiving the first transfer volume, a second transfer volume and a second retention volume from the first transfer volume, wherein said second separation mechanism comprises a width that is lesser than the width of the second chamber, and a length that is lesser than the length of the second chamber, said second separation mechanism is not in contact with the inner surface of the second chamber, and all of said first transfer volume flows through said second separation mechanism before entering into the second chamber;

a third chamber comprising a first side, a second side and one or more third separation mechanisms, wherein the first side is in fluid communication with the second chamber and configured to:
  receive the second transfer volume; and
  separate a third transfer volume and a waste volume from the second transfer volume, wherein said third separation mechanism comprises a length extending from said first side to said second side so that said third separation mechanism is flush with both said first and second sides, and all of said second transfer volume flows through said third separation mechanism before entering into the third chamber via a plurality of holes on said third separation mechanism;

a pump in fluid communication with at least the third chamber, wherein the pump is configured in a first state to establish a horizontal flow of the second transfer volume from the first side of the third chamber to the second side of the third chamber;

a waste collection repository in fluid communication with the second side of the third chamber via a first coupling and configured to receive the waste volume; and a product collection repository in fluid communication with the second side of the third chamber via a second coupling and configured to receive the third transfer volume, wherein the third transfer volume comprises a predetermined volume of cells and fluid.

2. The system of claim 1, wherein the first separation mechanism comprises pores with a first average pore size, wherein the first separation mechanism comprises a length from 5% to 50% of a length of the first chamber.

3. The system of claim 1, wherein the second separation mechanism comprises pores with a second average pore size, wherein the second average pore size is less than the first average pore size.

4. The system of claim 1, wherein the third separation mechanism comprises pores with a third average pore size, such that the third transfer volume comprises a plurality of cells of an average diameter greater than the third average pore size.

5. The system of claim 1, further comprising a sensor in communication with the pump wherein the pump, while configured in a second state, deactivates in response to a determination by the sensor that a predetermined volume of cells and fluid is present in the product collection repository.

6. The system of claim 5, wherein the sensor comprises an optic sensor.

7. The system of claim 5, wherein the sensor comprises a level sensor, and wherein the sensor is coupled to the pump.

8. A method of obtaining a target cell volume, comprising:
  separating, via a first separation mechanism in a first chamber of a cell separation apparatus, and when a pump coupled to the cell separation apparatus is in an activated state, a starting volume of biological materials into a first transfer volume and a first retained volume, said first separation mechanism is disposed in the first chamber to span an inner diameter of said first chamber so that all of said volume of biological materials flows through said first separation mechanism and not around said first separation mechanism;
  transferring the first transfer volume into a second chamber of the cell separation apparatus, wherein the second chamber is fluidly coupled to the first chamber;
  separating, via a second separation mechanism coupled to the second chamber, the first transfer volume into a second transfer volume and a second retained volume, wherein said second separation mechanism comprises a width that is lesser than the width of the second chamber, and a length that is lesser than the length of the second chamber, said second separation mechanism is not in contact with the inner surface of the second chamber, and all of said first transfer volume flows through said second separation mechanism before entering into the second chamber;
  transferring the second transfer volume into a third chamber of the cell separation apparatus, wherein the second chamber is fluidly coupled to the third chamber;
  separating, via one or more third separation mechanism coupled to the third chamber, the second transfer volume into a first cell volume, wherein said third separation mechanism comprises a length extending from a first side of the third chamber to a second side of the third chamber so that said third separation mechanism is flush with both said first and second sides, and all of said second transfer volume flows through said third separation mechanism before entering into the third chamber via a plurality of holes on said third separation mechanism, wherein separating the second transfer volume comprises performing at least one separation cycle;
  obtaining, subsequent to the at least one separation cycle, the first cell volume in the product collection repository.

9. The method of claim 8, wherein the at least one cell separation cycle comprises:
  introducing the second transfer volume in the third chamber, and
  establishing a horizontal flow through the third chamber from a first side of the third chamber to a second side of the third chamber,
  wherein a first portion of the second volume is passed through the third separation mechanism and into a waste repository, and
  wherein a second portion of the second volume is retained by the third separation mechanism and transferred into the product collection repository.

10. The method of claim 8, further comprising, determining, by a sensor coupled to the product collection repository, when the first cell volume is a target cell volume and, subsequent to the determination, removing the first cell volume from the product collection repository.

11. The method of claim 10, further comprising, subsequent to the removing, discarding the cell separation apparatus.

12. The method of claim 8, further comprising determining, by a sensor coupled to the product collection repository, when the first cell volume is not target cell volume and, subsequent to the determination, separating the first cell into the target cell volume via an at least one additional cell separation cycle.

13. The method of claim 10, further comprising changing, in response to the determination by the sensor that the target cell volume is reached, the pump from the activated state to an inactive state.

14. The method of claim 10, wherein each cycle of the plurality of separation cycles reduces the volume in the product collection repository until the target cell volume is reached.

15. The method of claim 8, further comprising cycling a predetermined volume of media through the second chamber during the separating for a predetermined number of cycles or for a predetermined time period during the separating in the second chamber.

16. A system for obtaining a target cell volume, comprising:
   a first chamber comprising an inner diameter and a first separation mechanism, wherein the first separation mechanism is configured to separate a volume of biological material into a volume of fibrous tissue and lipids and a first transfer volume, said first separation mechanism is disposed in the first chamber to span said inner diameter so that all of said volume of biological material flows through said first separation mechanism and not around said first separation mechanism;
   a second chamber in fluid communication with the first chamber, wherein the second chamber comprises a width, a length, an inner surface and a second separation mechanism that is configured to receive the first transfer volume from the first chamber and separate out a second transfer volume, said second separation mechanism comprises a width that is lesser than the width of the second chamber, and a length that is lesser than the length of the second chamber, said second separation mechanism is not in contact with the inner surface of the second chamber, and all of said first transfer volume flows through said second separation mechanism before entering into the second chamber;
   a third chamber in fluid communication with the second chamber, said third chamber comprises a first side, a second side, and one or more third separation mechanism, wherein said third separation mechanism comprises a length extending from said first side to said second side so that said third separation mechanism is flush with both said first and second sides, and all fluid received from the second chamber flows through said third separation mechanism before entering into the third chamber via a plurality of holes on said third separation mechanism;
   a waste repository in fluid communication with the third chamber;
   a product collection repository in fluid communication with the third chamber; and
   a pump, wherein the third separation mechanism is configured to separate the second transfer volume into a cell volume comprising solids larger than the holes of the third separation mechanism and a waste volume comprising solids smaller than the holes of the third separation mechanism, and wherein the pump in a first activated state establishes a flow through the third chamber such that the cell volume is transferred to the product collection repository and the waste volume is transferred to the waste repository.

17. The system of claim 16, wherein the first chamber comprises a syringe body and the first separation mechanism extends across an inner diameter of the syringe body and comprises from 5% to 50% of a volume of the syringe body.

18. The system of claim 16, wherein the first separation mechanism comprises an average pore size from about 50 µm to 200 µm, and wherein an average pore size of the second separation mechanism is less than the average pore size of the first separation mechanism.

19. The system of claim 16, wherein the third separation mechanism comprises a porous, hollow tube and an outside diameter that is less than an inside diameter of the third chamber.

20. The system of claim 16, wherein the third separation mechanism comprises a plurality of porous, hollow tubes.

* * * * *